United States Patent [19]

Brown et al.

[11] Patent Number: 4,583,795
[45] Date of Patent: Apr. 22, 1986

[54] CRASH CART FOR USE IN A HOSPITAL AND THE LIKE

[76] Inventors: Rollen E. Brown; M. Sue Brown, both of 1378 S. Fairfax, Denver, Colo. 80222

[21] Appl. No.: 567,775

[22] Filed: Jan. 3, 1984

[51] Int. Cl.⁴ ............................................. A47B 81/00
[52] U.S. Cl. ................... 312/209; 312/249; 312/285
[58] Field of Search ............ 312/249, 252, 285, 140.2, 312/209, 26, 30, 123, 125, 283, 3, 217, 257 A, 117, 11, 197, 305, 202; 108/103

[56] References Cited

U.S. PATENT DOCUMENTS

| | | | |
|---|---|---|---|
| 139,419 | 5/1873 | Payne | 312/202 |
| 662,014 | 11/1900 | McNamara | 312/3 |
| 845,707 | 2/1907 | Randolph | 312/285 |
| 1,115,899 | 11/1914 | Clouser | 312/305 |
| 1,371,944 | 3/1921 | Sterling et al. | 312/202 |
| 1,448,253 | 3/1923 | Bodker | 312/202 |
| 1,677,544 | 7/1928 | Brainard et al. | 357/217 |
| 1,883,961 | 10/1932 | Kosmerl | 312/252 |
| 4,054,343 | 10/1977 | Heyland | 312/209 |
| 4,127,311 | 11/1978 | Weiman | 312/234.3 |
| 4,448,463 | 5/1984 | Amos | 312/257 A |

Primary Examiner—William E. Lyddane
Assistant Examiner—Gerald Anderson
Attorney, Agent, or Firm—Edwin H. Crabtree

[57] ABSTRACT

A crash cart for use in storing equipment and drugs in a hospital emergency room, intensive care unit and other areas. The cart is characterized by being easily movable and readily accessible into all sides of the cart for quickly viewing and removing equipment and drugs during a crisis situation.

7 Claims, 4 Drawing Figures

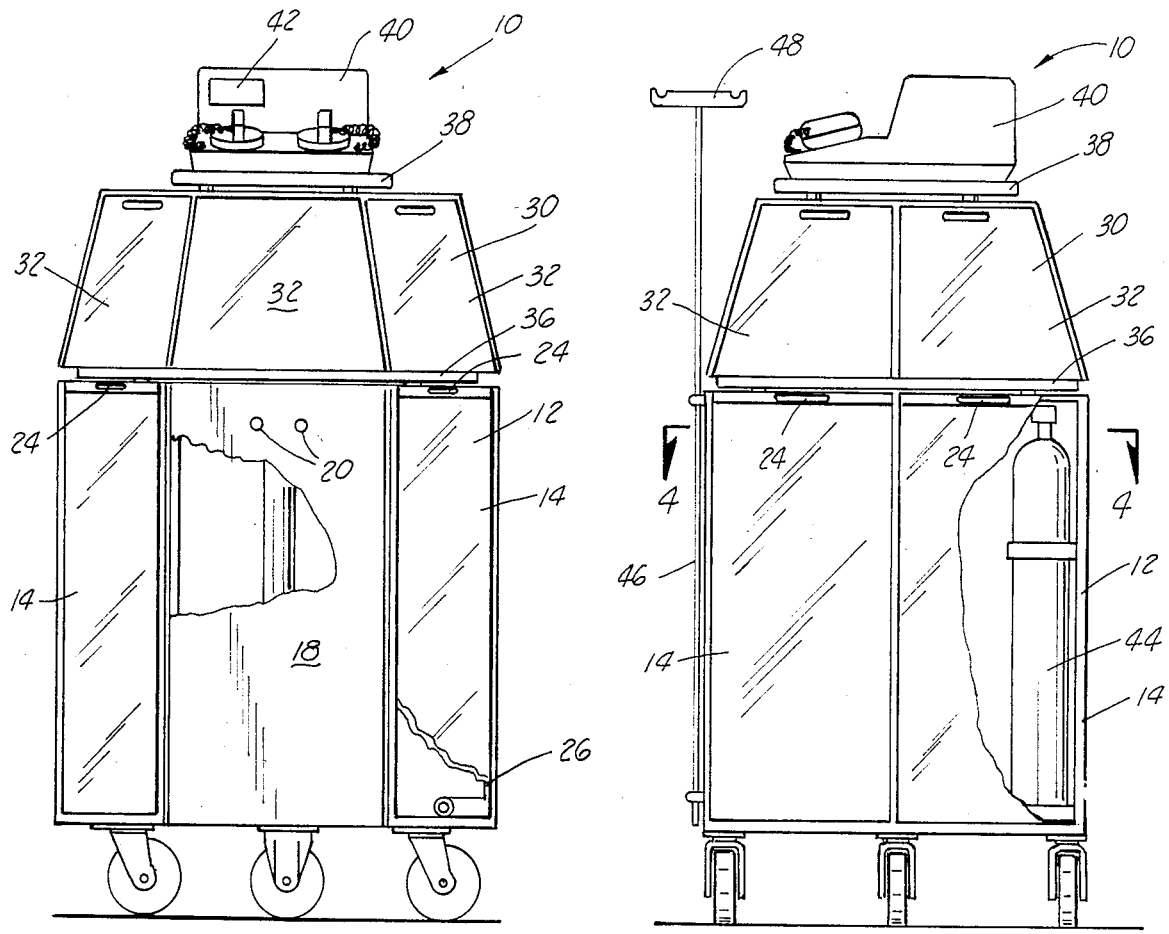
FIG. 1
FIG. 2
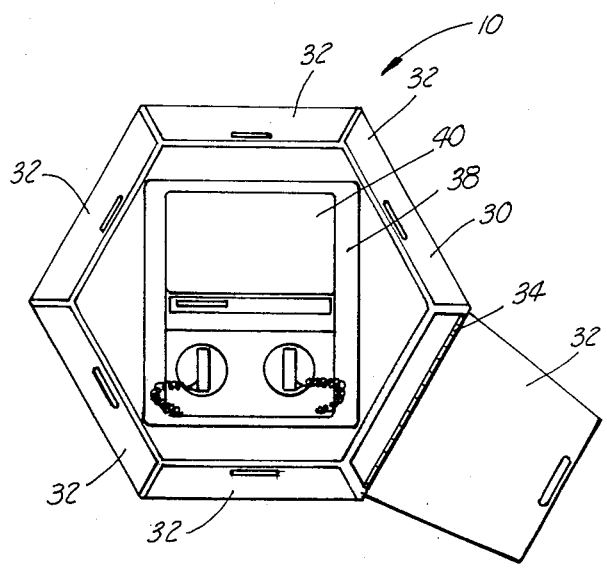
FIG. 3
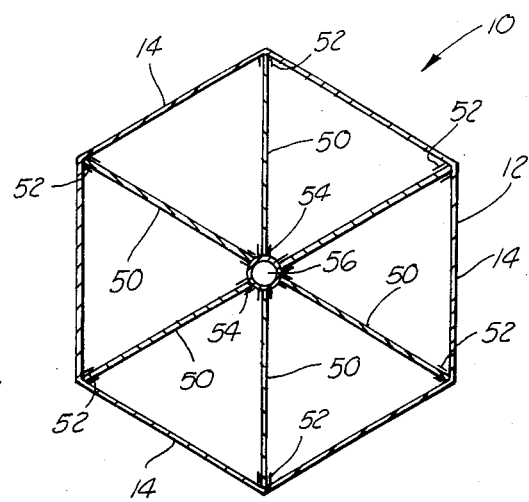
FIG. 4

CRASH CART FOR USE IN A HOSPITAL AND THE LIKE

BACKGROUND OF THE INVENTION

This invention relates to a cart for storing equipment and drugs therein and more particularly but not by way of limitation to a crash cart for use in hospital emergency rooms, intensive care units and other areas wherein it is necessary to quickly remove equipment and drugs required during an emergency situation.

In hospital emergency rooms, intensive care units and other areas, core zero or cardiac arrest is quite common. When this occurs immediate care must be provided in minutes to prevent permanent brain cell damage. To speed the delivery of necessary drugs and equipment, mobile carts are used by designated teams of nurses and doctors.

Heretofore, common table top equipment tool boxes were used made of stainless steel with rubber tire caster wheels and having several drawers containing drugs and resuscitation equipment. Some of the more quickly needed equipment were hung on the side of the cart and a defibrillator monitoring unit was mounted on top of the equipment box.

Because of the number of personnel on an emergency team and the necessity for speed in the delivery of care, confusion quite often occurs when the first drugs to be administered were in one drawer while an equally important piece of equipment was in another drawer. Because of the structure of the equipment box access to more than one drawer at a time was impossible causing serious delays.

Further these carts were organized in as much as first used drugs were in a specific drawer, respirator equipment in another drawer etc. This means one drawer after another must be opened and closed repeatedly when assisting the nurse or physician.

In U.S. Pat. No. 1,015,664 to Booth, U.S. Pat. No. 3,428,383 to Nobel, U.S. Pat. No. 3,828,695 to Skarky, U.S. Pat. No. 3,969,006 to Brown, U.S. Pat. No. 4,114,965 to Oye et al. and U.S. Pat. No. 4,127,311 to Weiman various types of wheeled emergency carts and emergency cabinets are disclosed. None of these prior art carts specifically disclose the unique features and advantages of the subject invention as described herein.

SUMMARY OF THE INVENTION

The subject invention provides ready access at the same time into a crash cart from all sides. The crash cart may be hexangle in shape with caster wheels arranged so it can be easily turned on a central axis. Each of the sides are readily accessible at the same time with one of the sides being quickly removable for use as a cardiac arrest board which is placed under the patient's back during resuscitation.

The invention further includes a horizontal rotatable shelf mounted on the top of the cart for mounting a defibrillator and monitor thereon so it can be turned independently and seen by the lead physician at all times.

The cart is made of aluminum and plastic for lightweight and maneuverability. The sides of the cart are transparent panels which are color coded so equipment and drugs stored inside can be quickly identified and removed.

After an emergency the removable panels can be quickly entered for restocking and made ready for use again in a few minutes.

Further the upright shape of the cart provides better mobility and requires less floor space than conventional rectangular shaped equipment boxes and carts. This is extremely important considering the congestion usually surrounding a patient during emergencies.

The crash cart for use in storing equipment and drugs in a hospital and the like includes a lower housing having caster wheels mounted on the bottom thereof. The lower housing has side panels which may be opened for entrance into the housing. One or more of the side panels may be transparent for viewing the items stored therein. An upper housing is mounted on top of the lower housing with the upper housing having one or more transparent side panels for viewing items stored therein. The side panels may be opened for entrance into the housing. A flat rotatable shelf is mounted on top of the upper housing and is adapted for receiving equipment such as a defibrillator thereon.

The advantages and objects of the invention will become evident from the following detailed description of the drawings when read in connection with the accompanying drawings which illustrate preferred embodiments of the invention.

BRIEF DESCRIPTION OF THE DRAWINGS

FIG. 1 is a front view of the crash cart.
FIG. 2 is a side view of the crash cart.
FIG. 3 is a top view of the crash cart.
FIG. 4 is a top sectional view of the crash cart taken along lines 4—4 shown in FIG. 2.

DETAILED DESCRIPTION OF THE DRAWINGS

In FIG. 1 the crash cart for use in storing equipment and drugs in a hospital and the like is designated by general reference numeral 10. The cart 10 includes a lower housing 12 having a plurality of caster wheels 14 mounted on the bottom thereof. The lower housing 12 has angular shaped side panels 14 disposed therearound for entrance into all sides of the housing 12. The side panels 14 may be transparent and color coded for ready access into a particular compartment inside the housing 12. One of the panels 14 may be an angular shaped cardiac arrest board 18 having a pair of finger holes 20 in the top thereof so the board 18 can be quickly removed from the housing 12 for use in placing behind a patient's back during a cardiac arrest.

As mentioned above one or more of the side panels 14 of the lower housing 12 may be transparent and may also be made of a flexible material formed into a roll 22 as shown in a cut-away portion of the panel 16 on the right side of the drawing. By gripping a handle 24 at the top of panel 14 the flexible material of the panel 16 is guided downwardly in guides 26 in the side of the housing 12 and into the roll 22. By lowering the panel 14 into the roll 22 access into the housing is quickly gained without having any outwardly extending protrusion which would cause an obstruction during a crisis situation.

Mounted on top of the lower housing 12 is an upper housing 30 having side panels 32 therearound which may be also transparent and angular in shape for viewing items stored therein. The side panels 32 may be color coded and are hinged at the bottom by a hinge 34 as shown in FIG. 3. The side panels 32 may be lowered into a horizontal position for storing drugs and placing equipment thereon.

The upper housing 30 may be secured to the top of the lower housing 12 or may be mounted on a flat rotatable shelf 36 which allows the upper housing 30 to be rotated independently of the lower housing 12 for ready access into a particular compartment in the upper housing 30.

The crash cart 10 also includes a flat rotatable shelf 38 mounted on top of the upper housing 30 for receiving a defibrillator 40 or any other similar type of equipment used in a crisis situation. By mounting the defibrillator 40 on the rotatable shelf 38, ready access of a view screen 42 is always within the sight of the attending physician.

In FIG. 2 a side view of the cart 10 is shown with a portion of one of the panels 14 of the lower housing 12 shown in a cut-away view to expose oxygen equipment 44 stored therein. Also a telescoping rod 46 with bracket 48 is shown attached to the side of the housing 12 for holding an intravenous bottle.

In FIG. 3 a top view of the cart 10 is shown with the defibrillator 40 shown mounted on the top of the angular shaped rotatable shelf 38. Also seen in this view is one of the panels 32 of the upper housing 30 lowered into a horizontal position for receiving drugs or equipment thereon.

In FIG. 4 a top sectional view of the cart 10 is shown taken along lines 4—4 shown in FIG. 2. In this view the lower housing 12 can be seen with removable partitions 50 which slide into vertical grooves 52 adjacent the side panels 14 and grooves 54 extending outwardly from a center circular post 56. The partitions 50 may be removed to increase the size of a particular compartment in the housing depending on the size of the equipment and space needed in any of the compartments. While it is not shown in the drawings the upper housing 30 likewise can include removable partitions similar to the partitions 50 shown in FIG. 4.

While the cart 10 is shown having a hexagonal shape with the upper housing 30 and lower housing 12 each having six side panels, it can be appreciated that various angular shapes can be used equally well for gaining entrance into all sides of the cart without departing from the spirit or scope of the invention.

Changes may be made in the construction and arrangement of the parts or elements of the embodiments as described herein without departing from the spirit or scope of the invention defined in the following claims.

What is claimed is:

1. A crash cart for use in storing equipment and drugs in a hospital and the like, the cart comprising:
    a lower housing having caster wheels mounted on the bottom thereof, the lower housing having angular-shaped side panels therearound which may be opened for entrance into all sides of the housing, one or more of the side panels being transparent for viewing the items stored therein and made of a flexible material which is lowered and rolled into a roll in the bottom of the housing for entrance into the housing;
    an upper housing mounted on top of the lower housing, the upper housing having one or more transparent angular shaped side panels therearound for viewing items stored therein, the side panels hinged to the bottom of the housing so the panels when opened may be lowered into a horizontal position for entrance into all sides of the housing and used as shelves for dispensing drugs or laying equipment thereon; and
    a first flat horizontal rotatable shelf mounted on top of the upper housing, the shelf adapted for receiving equipment such as a defibrillator thereon.

2. The cart as described in claim 1 wherein one of the side panels of the lower housing is an angular-shaped board which is removable from the housing for use as a cardiac arrest board.

3. A crash car for use in storing equipment and drugs in a hospital and the like, the cart comprising:
    a lower housing having caster wheels mounted on the bottom thereof, the lower housing having angular-shaped side panels therearound which may be opened for entrance into all sides of the housing, one or more of the side panels being transparent for viewing the items stored therein and made of a flexible material which is lowered and rolled into a roll in the bottom of the housing for entrance into the housing;
    an upper housing mounted on top of the lower housing, the upper housing having one or more transparent angular shaped side panels therearound for viewing items stored therein, the side panels hinged to the bottom of the housing so the panels when opened may be lowered into a horizontal position for entrance into all sides of the housing and used as shelves for dispensing drugs or laying equipment thereon;
    a first flat horizontal rotatable shelf mounted on top of the upper housing, the shelf adapted for receiving equipment such as a defibrillator thereon; and
    a second flat horizontal rotatable shelf attached to the top of the lower housing and receiving the upper housing thereon, the shelf allowing the upper housing to be rotated on top of the lower housing.

4. The cart as described in claim 3 wherein the upper and lower housings include partitions therein for dividing the two housings into individual compartments.

5. The cart as described in claim 4 wherein the partitions are removable for enlarging the sizes of the compartments.

6. The cart as described in claim 3 wherein the side panels of the upper and lower housings are color-coded for aid in identifying certain compartments in the housing having the desired equipment stored therein.

7. The cart as described in claim 3 wherein the upper and lower housings are hexangle in shape with the lower housing and upper housing each having six side panels which may be opened for entrance therein.

* * * * *